US 6,737,076 B2

(12) United States Patent
Fritsche et al.

(10) Patent No.: US 6,737,076 B2
(45) Date of Patent: May 18, 2004

(54) HYPOALLERGENIC COMPOSITION CONTAINING TOLEROGENIC PEPTIDES

(75) Inventors: Rodolphe Fritsche, La-de-Tour Peilz (CH); Sophie Pecquet, Lausanne (CH); Lionel Bovetto, Larringes (FR); Francoise Maynard, Kehrsatz (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/907,109

(22) Filed: Jul. 16, 2001

(65) Prior Publication Data

US 2002/0037357 A1 Mar. 28, 2002

Related U.S. Application Data

(63) Continuation of application No. PCT/EP00/00334, filed on Jan. 17, 2000.

(30) Foreign Application Priority Data

Jan. 19, 1999 (EP) .............................................. 99200130

(51) Int. Cl.[7] .............................................. A61K 47/00
(52) U.S. Cl. ...................... 424/439; 424/400; 424/489; 424/499
(58) Field of Search ................................ 424/400, 439, 424/489, 499

(56) References Cited

U.S. PATENT DOCUMENTS 5,039,532 A    8/1991   Jost et al. ..................... 426/41

FOREIGN PATENT DOCUMENTS

| EP | 0 629 350  | 12/1994 |
| EP | 0 827 697  | 3/1998  |
| JP | 07 138187  | 5/1995  |

OTHER PUBLICATIONS

R. Fritsché, "Induction of Oral Tolerance to Cow's Milk Proteins in Rats Fed With a Whey Protein Hydrolysate", Nutrition Research, vol. 18, No. 8, pp. 1335–1341 (1998).
C. Lo et al., "Infant formula, past and future: opportunities for improvement", American Journal of Clinical Nutrition, vol. 63, No. 4, pp. 646S–650S (1996).
C. Nicodemus et al., "Integrated Clinical Experience with Tolerogenic Peptides", Int Arch Allergy Immunol, 113, pp. 326–328 (1997).

Primary Examiner—Thurman K. Page
Assistant Examiner—Charesse Evans
(74) Attorney, Agent, or Firm—Winston & Strawn LLP

(57) ABSTRACT

A hypoallergenic composition for the induction of protein tolerance in at risk individuals of protein allergy. The composition contains (i) a "non allergenic" protein extensively hydrolyzed basis and/or of (ii) a free amino acid basis. The composition contains, as an active ingredient, at least one tolerogenic peptide of the allergenic protein.

16 Claims, 2 Drawing Sheets

Figure 1:
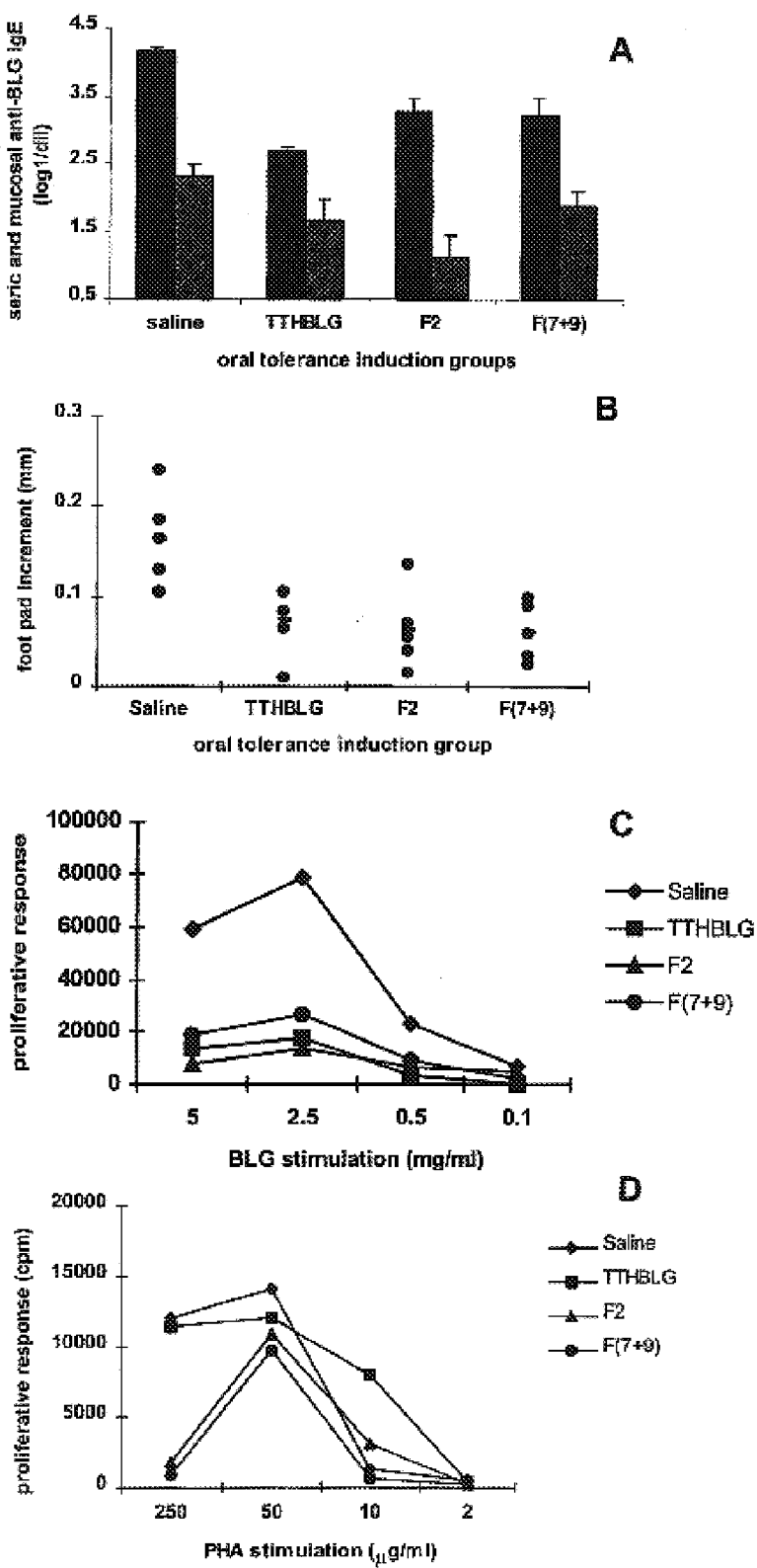

Peptide T1  H₂N-A-L-K-COOH      Peptide T2  H₂N-H-I-R-COOH   Peptide T3  H₂N-F-D-K-COOH
(139-141)                       (146-148)                    (136-138)

Peptide T4  H₂N-I-I-A-E-K-COOH        Peptide T5  H₂N-E-N-G-E-C-A-Q-K-COOH
(71-75)                               (62-69)

Peptide T6  H₂N-I-D-A-L-N-E-N-K-COOH    Peptide T7  H₂N-G-L-D-I-Q-K-COOH
(84-91)                                 (9-14)

Peptide T8  H₂N-A-L-P-M-COOH       Peptide T9, T10, T11  H₂N-W-E-N-G-E-C-A,-Q,-K,-COOH
(142-145)                          (61-67,-68,-69)

Peptide T12  H₂N-T-P-E-V-D-D-E-A-L-E-K-COOH        Peptide T13  H₂N-L-I-V-T-Q-T-M-K-COOH
(125-135)                                          (1-8)

Peptide T14  H₂N-A-L-P-M-H-I-R-COOH        Peptide T15  H₂N-I-P-A-V-F-K-COOH
(142-148) = T8 (142-145) + T2 (146-148)    (78-82)

Peptide T16  H₂N-V-A-G-T-W-Y-COOH          Peptide T17  H₂N-V-L-V-L-D-T-D-Y-K,-K-COOH
(15-20)                                    (92-99,100)

Peptide T18  H₂N-T-P-E-V-D-D-E-A-L-E-K-F-D-K-COOH
(125-138) = T12 (125-135) + T3 (136-138)

Peptide T19  H₂N-A-A-S-D-I-S-L-L-D-A-Q-S-A-P-L-R-COOH
(25-40)

Peptide T20, T21                    H₂N-W,-E-N-G-E-C-A-Q-K-COOH
(61, 62-69):S-S:(149-162)                         |
                                    H₂N-L-S-F-N-P-T-Q-L-E-E-Q-C-H-I-COOH Peptide T22  H₂N-S-L-A-M-A-A-S-D-I-S-L-L-D-A-Q-S-A-P-L-R-COOH
(21-40)

Peptide T23  H₂N-V-Y-V-E-E-L-K-P-T-P-E-G-D-L-E-I-L-L-Q-K-COOH
(41-60)

Peptide T24  H₂N-L-S-F-N-P-T-Q-L-E-E-Q-C-H-I-COOH
(149-162)

Figure 2

HYPOALLERGENIC COMPOSITION CONTAINING TOLEROGENIC PEPTIDES

CROSS-REFERENCE TO RELATED APPLICATIONS

This application is a continuation of the U.S. national phase designation of International Application no. PCT/EP00/00334 filed Jan. 17, 2000, the content of which is expressly incorporated herein by reference thereto.

FIELD OF THE INVENTION

This invention relates to a hypoallergenic composition containing specific tolerogenic peptides of proteins, wherein the composition can induce oral tolerance to the native proteins. It also relates to the use of tolerogenic peptides of milk protein for the preparation of a composition inducing immunological tolerance to milk proteins.

BACKGROUND OF THE INVENTION

During the common process of nutrition, dietary proteins are presented to the immune system via the gut, followed by an immune unresponsiveness to the ingested nutrients. This vital phenomenon, called oral tolerance, is efficient for the large majority of people. If oral tolerance fails, food allergy occurs, requiring the strict avoidance of the incriminated food.

Targeted food avoidance represents a hard task for adult patients with food allergy. For example, to strictly remove cow's milk from the diet of allergic infants might be even more difficult, especially if breastfeeding is not possible or desired.

The allergies to cow's milk and to the formulas containing cow's milk adapted to the needs of infants are due to the fact that the proteins of cow's milk differ from the proteins of mother's milk and can constitute allergens. Among whey proteins, β-lactoglobulin is the major component and is a strong allergen.

Besides breastfeeding, the primary recommendation for prevention, hypoallergenic formulae are systematically prescribed to "at risk" newborns, namely asymptomatic infants with atopic parents.

In contrast to adapted formulae, cow's milk proteins have been hydrolyzed in hypoallergenic formulae, to decrease the potential allergenicity. This approach has been demonstrated to be efficient in order to prevent sensitization by native proteins present in the adapted formulae.

Thus, in U.S. Pat. No. 4,293,571 a protein hydrolysate was prepared by pancreatic hydrolysis, coagulation of non-hydrolyzed proteins by a heat treatment and ultrafiltration to eliminate the coagulated residual proteins and the macropeptides that could constitute allergens. Also, U.S. Pat. No. 5,039,532 provides an improved process for the preparation of a hydrolysate of animal milk proteins substantially reduced in allergens, in which a whey product was subjected to enzymatic hydrolysis.

Two different types of hypoallergenic formulae are proposed to high-risk babies: partially and extensively hydrolyzed formulae, differentiated by the extent of hydrolysis of the native proteins. But as is clear from the art cited above, the primary focus to date in dealing with allergies to cow's milk has been to find preparations that will not induce an allergic response, i.e. to provide non-allergenic formulations. Nonetheless, while such formulations have permitted a person allergic to cow's milk to avoid an allergic response, they do not solve the problem which is to enable a person to drink unaltered milk products.

More recently, it has been investigated that partially hydrolyzed milk formulations are not only of reduced allergenicity but can induce immunological tolerance to milk proteins (see, e.g., European patent application 0 827 679). Extensively hydrolyzed formulae are specially designed for treating patients allergic to cow's milk proteins but their ability to induced long-term oral tolerance is questioned.

Thus, European patent application 0 629 350 discloses the use of non-allergenic whey protein hydrolysates which are said to be capable of inducing cow's milk protein tolerance. Although this patent application indicates that whey protein hydrolysates substantially free of allergenic proteins could be used to induce cow's milk protein tolerance in children at risk of cow's milk allergy, the present inventors found on analyzing other non-allergenic whey protein hydrolysates that non-allergenicity did not necessarily translate into the ability to induce cow's milk protein tolerance. Indeed, some of the formulations exhibiting the highest degree of non-allergenicity were found to be unsuitable for inducing cow's milk protein tolerance.

Although Lo, C. W. and Kleiman, R. E. (American Journal of Clinical Nutrition 1996, 63 (4), 646S-650S) suggest that infant formula containing tolerogenic peptides could be used for treating allergic diseases or suppressing the development of autoimmune disorders, it is clear that the art lacked the information to provide formulae that would be the most suitable for tolerance induction The present invention now overcomes the shortcomings of the art.

SUMMARY OF THE INVENTION

This invention relates to a hypoallergenic composition for the induction of protein tolerance in at risk individuals of protein allergy. The composition contains (i) a "non-allergenic" extensively hydrolyzed proteins basis and/or (ii) a free amino acid basis, and comprises as the active ingredient at least one tolerogenic peptide of the allergenic protein.

In a preferred embodiment, the tolerogenic peptide is present in the form of (i) one or more isolated tolerogenic peptidic fractions of hydrolysis of proteinaceous material containing the allergenic protein, and/or (ii) one or more synthetically prepared tolerogenic peptides.

This composition also contains a source of nitrogen which may provide 7 to 25% of the total energy, a source of carbohydrates which may provide at least 28 to 66% of the total energy, a source of lipids which may provide at least 25 to 60% of the total energy and at least one tolerogenic peptide of the different proteins.

A major advantage of this composition is to induce oral tolerance in "at risk" individuals, in order to avoid eventual sensitization by use of native tolerogens. Moreover, the tolerogenic peptides derived from protein hydrolysis offer both hypoallergenic and tolerogenic properties and induce oral tolerance at the humoral and cellular levels.

This composition is particularly intended for individuals at risk of milk protein allergy.

Another aspect of the present invention is the use of tolerogenic peptides of milk proteins for the preparation of a hypoallergenic composition intended for mammals susceptible to cow's milk allergy.

In a preferred embodiment, tolerogenic peptides are from milk origin and particularly from β-Lactoglobulin (β-LG), α-lactalbumin, bovin serum albumin or casein origin.

For the preparation of the composition, tolerogenic peptides may be used in the form of peptidic fractions containing the following peptides: H₂N-I-D-A-L-N-E-N-K-COOH, H₂N-V-L-V-L-D-T-D-Y-K,-K-COOH or H₂N-T-P-E-V-D-D-E-A-L-E-K-F-D-K-COOH from β-Lactoglobulin.

In another aspect, the invention provides a method for the preparation of tolerogenic peptides useful in the induction of protein tolerance in at risk individuals to protein allergy, wherein:
(i) a proteinaceous material containing the allergenic protein is hydrolyzed to a degree of hydrolysis of about 10 to 50%;
(ii) then treated to inactivate residual enzyme activity; and
(iii) the protein hydrolysate solution is clarified and submitted to precipitation treatment or passed into a chromatography column filled with appropriated resin to extract the tolerogenic peptidic fractions.

DETAILED DESCRIPTION OF THE PREFERRED EMBODIMENTS

In the present invention, the term tolerance is to be understood as a state of specific immunological unresponsiveness. Both humoral (antibodies) and cell-mediated (lymphocyte . . . ) pathways of the immune response may be suppressed by tolerance induction. A breakdown of oral tolerance is considered to be the underlying cause of food allergy.

The term "allergen" is to be understood as a protein or macropeptide capable of initiating allergic reactions in humans, particularly at risk infants or nurslings. Infants are considered being "at risk" of protein allergy when either one or two parents or one sibling is atopic.

The term "tolerogenic peptide" is to be understood as a proteic fragment or fragments corresponding to parts of the native protein, sized from 200 to 6000 Daltons ("Da"), corresponding to about 3 to 50 amino acids, and preferably between 500 to 3000 Da and being able to induce specific oral tolerance to native proteins.

The term "non-allergenic basis" is to be understood as a nitrogen source containing a well-balanced amino-acids composition. The "non-allergenicity" is defined for milk proteins as residual allergenicity of individual whey proteins not exceeding 1 ppm and as residual allergenicity of total caseins not exceeding 10 ppm.

The hypoallergenic composition may contain as a source of nitrogens, peptides or free amino acids and particularly from milk proteins such as whey proteins, α-lactalbumin, β-lactoglobulin, bovine serum albumin, casein acid, caseinates, or α, β, κ-casein, for example. The source of nitrogen can provide at least 7 to 25% of the total energy.

As a source of carbohydrates, lactose, saccharose, starch or maltodextrin may be used. Carbohydrates may provide at least 28 to 66% of the total energy.

Vegetable oils or butter oil are preferably used as a source of lipids that may provide at least 25 to 60% of the total energy.

Vitamins, oligoelements and minerals can be added in an amount sufficient to meet daily requirements.

The composition according to the present invention comprises as the active ingredient at least one tolerogenic peptide of the allergenic protein, wherein the tolerogenic peptide has been selected for its ability to induce oral tolerance.

The tolerogenic peptides can be obtained by enzymatic hydrolysis of proteinaceous material containing the allergenic proteins that are responsible for allergies in at risk individuals, followed by isolation of tolerogenic peptidic fractions. These peptidic fractions enriched in said tolerogenic peptides can be obtained by separation of the protein hydrolysate. The tolerogenic peptides may also be present in the composition in the form of synthetically prepared tolerogenic peptides.

The composition contain an amount sufficient to induce oral tolerance which is preferably the one which allows a complete oral tolerance induction, namely the one which prevents from any reaction after DBPCFC (double blind placebo controlled food challenge) performed with cow's milk. Accordingly, tolerogenic peptides may be present in an amount of about 0.01% to 10% (nitrogen source of the protein), for example and preferably about 0.1 to 0.2% of total peptides.

In the particular case of tolerance to milk proteins, the composition may contain tolerogenic peptides from milk origin such as—lactoglobulin or caseins, for example. Tolerogenic peptides may thus be in the form of a peptidic fraction comprising at least one of the following peptides: H₂N-I-D-A-L-N-E-N-K-COOH, H₂N-V-L-V-L-D-T-D-Y-K,-K-COOH or H₂N-T-P-E-V-D-D-E-A-L-E-K-F-D-K-COOH from-β-lactoglobulin.

In a preferred embodiment, a method for the preparation of tolerogenic peptides comprises the following steps:
(i) a proteinaceous material containing the allergenic protein is hydrolyzed to a degree of hydrolysis of about 10 to 50%;
(ii) then treated to inactivate residual enzyme activity; and
(iii) the protein hydrolysate solution is clarified and submitted to precipitation treatment or passed into a chromatography column filled with appropriated resin and tolerogenic peptidic fractions are recovered.

This preferred method is well suited to treatment of hydrolysates prepared from various protein concentration (Ntot %=N * 6.38) for modifying the ratio of tolerogenic activity by residual antigenicity from proteinaceous material. If one defines arbitrarily the antigenicity of a native protein to be $10^6$ (as $10^6 \mu g/g$ of protein), and the tolerogenic response to be 1, then, for a native protein, this ratio is $10^{-6}$. Therefore, the ratio qualifying the tolerogenic activity of one given fraction or tolerogenic peptide should be at least $2 \times 10^{-2}$.

The proteinaceous material to be treated may be any composition containing protein material and in particular solution or dispersion of milk proteins: whey proteins, acid whey protein, sweet whey proteins, whey protein concentrates, whey protein isolate, demineralized whey powder or caseinates, for example.

In general, the protein content may vary within the range of about 70 to 95% by weight but the starting material is preferably as rich in protein as possible.

The proteins present in the proteinaceous material can be modified with proteolytic enzymes into protein hydrolysate having a degree of hydrolysis (α-amino-N/Ntot) of preferably about 10–50%.

The proteolytic enzymes may be for example, from animal or vegetable origins (pepsin, chymotrypsin, trypsin, intestinal mucosa extract, pancreatic extracts, chymosin, papain, bromelain, ficin), bacterial or fungi origins (serine and metalloproteases from *Bacillus subtilis, Bacillus licheniformis, Aspergillus orysae, Aspergillus wentii* and acidic proteases from *Aspergillus orizae, Aspergillus wentii, Mucor miehei, Mucorpusillus, Endothia parasitica*) or a combination of these.

During hydrolysis, concentration of proteinaceous material in solution or in suspension is preferably around 5–20% by weight and could be pasteurized before introducing proteases. The ratio enzyme/protein may be 0.1–10% weight/weight and preferably of about 0.25 to 4%.

Hydrolysis may be conducted at a temperature of about 35° C. to 65° C., during 30 minutes to 10 hours, preferably 30 min to 4 hours at pH values within the range 2.5 to 11, preferably 4.5, 7.0, 8.0, and 8.5. If desired the pH of the solution can be adjusted and regulated with citric acid, food grade HCl or NaOH, $NH_4OH$, KOH, Ca $(OH)_2$ for instance at a concentration of 2N pure or in blend.

Then, the protein hydrolysate may be submitted to a heat treatment of about 0.1 to 10 min at a temperature of about 70 to 110° C. to inactivate residual enzymes (i.e., proteases).

The protein hydrolysate solution thus obtained can be clarified by centrifugation and/or ultrafiltration to remove insoluble and intact proteins respectively, and the clear solution is recovered. It is possible to use at industrial scale different type of membranes (spiral, tubular, flat, allow fibers) made with different materials (minerals, polysulfone, . . . ) and having different cut off limits between 1,000 and 100,000 Daltons. Depending on the type of enzyme, the hydrolysis conditions and the type of membranes the modification of the tolerogenic fractions should be sufficient at this step.

The recovered clear hydrolysate solution can, if desired, be concentrated by evaporation to a dry solid content of 10–50% for a subsequent treatment or spray dried if enrichment in tolerogenic peptides is sufficient.

The protein hydrolysate solution thus obtained can be submitted to precipitation treatment by solvent, acid, or salts, for example, followed by a centrifugation. In the precipitation treatment, concentration of hydrolysate solution increases the yield and reduces the quantities of solvent. For example, ethanol may be added to obtain a final concentration within 15–60% volume/volume at a temperature of about 4° C. to 25° C. After one hour of incubation, a centrifugation (30 min at 4500 g) should separate soluble and insoluble peptides. Depending on the proteolysate, an acid (phosphoric or hydrochloric, for example) or phosphocalcic precipitation can be used. Then, solvents can be removed by evaporation and salts by electrodialysis.

The clear solution and the insoluble fraction are preferably recovered.

The protein hydrolysate solution thus obtained may be passed into a column filled with adsorption, ion exchange or hydrophobic resin at a flow rate of 0.1–4 column volumes per hour at a temperature of about 4° C. to 60° C. Before the chromatography treatment, the protein hydrolysate can be concentrated to provide a solution having a dry solid content of 8–35% by weight.

During chromatography, a fraction of peptide is absorbed into the resin by passing the hydrolysate solution into a column filled with the convenient support at a rate of 0.1–4 column volumes per hour. It is possible to use at industrial scale the different types of chromatography as: ion exchange, hydrophobic interactions, reverse phases, adsorption (hydroxyapatite, active charcoal, polystyrene base hydrophobic resins . . . ) or covalent chromatography.

In the chromatography treatment, the amount of hydrolysate solution per liter of resin filled column can be as high as 5 liters with the respect to dry solids of 10%. Preferably, a hydrolysate solution having 20–1000 g of dry solid per liter of resin is passed into the resin filled column. The chromatography treatment may be carried out at a pH of about 2 to 10 preferably 6–8, for the clarified hydrolysate solution. The chromatography treatment can be conducted at a temperature of about 4° C. to 60° C.

For example, the chromatography treatment to select tolerogenic fractions from β-lactoglobulin may consist in using:
- a strong cationic resin equilibrated with 0.1 N HCl at a flow rate of 1 volume/hour. The non-retained fraction was eluted with 3 volumes of water, the second fraction (fraction containing tolerogenic peptides) was eluted with 0–0.5 N NaOH, and the third fraction was eluted with 0.1 N HCl.
- a reverse phase (C18) resin equilibrated with pure water. Non retained fraction was eluted with water, then step by step (20% and 40% of ethanol) the second and the third were recovered.
- a strong anionic resin equilibrated with 0.1N NaOH. Non retained fraction was eluted by 3 volumes of water. The second fraction was eluted with 0.5N HCl, the third one with 0.1 N NaOH.

The most preferred method is to treat with resin a neutral solution, in that case, no pH adjustment is required-after hydrolysis step and the salt content of the product will be lower.

To conclude the chromatography treatment, the column can be eluted with pure water, then water containing salts, buffer, acids, bases, or organic solvents at a temperature of 4–60° C. Elution is realized step by step or by a gradient of concentration. The solutions that have passed through the column are recovered. If necessary, salts, solvents, acids, bases, are removed from the recovered solution, and the recovered solutions can be concentrated to a dry solids content of 35–65% and spray dried.

These peptides are then specific fragments corresponding to a part of the native protein sequence or to a part of the specific tryptic peptides of hydrolyzed protein.

These tolerogenic peptides can be used for the preparation of a composition inducing oral tolerance to native proteins, said composition is intended for mammals susceptible to protein allergy and particularly human and pets.

BRIEF DESCRIPTION OF THE DRAWING FIGURES

FIG. 1 represents specific oral tolerance induction in mice fed once with either TTH β-LG, F2 or F(7+9). A: Humoral (dark bars) and mucosal (gray bars) anti-β-LG IgE response. B: β-LG-specific DTH response (●) are individual foot pad increments and (–) are means from 10 mice per group. C and D: Specific (β-LG) and non specific (PHA) proliferative responses of splenic cells. Splenic lymphocytes from mice fed with either saline (♦), TTH β-LG (■), F2 (▲), or F (7+9) (●) were isolated and subsequently stimulated with decreasing concentrations of antigens. $^3H$ thymidine incorporation was measured after 120 hours of culture. ($^3H$)Tdr incorporation results were expressed in cpm, as a mean of triplicate cultures, the blank-subtracted mean was then plotted respectively against β-LG or PHA concentration.

FIG. 2 represents primary sequences assigned to tryptic peptides identified in β-Lactoglobulin hydrolysate. Vertical bar represents disulfide bond.

EXAMPLES

The following examples are given by way of illustration only and in no way should be construed as limiting the subject matter of the present application.

Example 1

Selection and Characterization of the Tolerogenic Peptides of β-Lactoglobulin

In the first following example, experiments were performed to select the tolerogenic peptides of β-LG.

β-LG was digested by TPCK treated typsin in conditions selected to provoke its mild digestion. The size and the molecular weight distribution of the resulting peptides from our β-LG hydrolysis model, respectively ranged from two to twenty-three aminoacids, and from 247 to 2719 Da. The tolerogenic properties of the resulting peptides have been assayed in an oral tolerance experimental mouse model Methods a) Animals Female Balb/c mice were obtained from IFFA-Crédo (L'Abresle, France). They were all bred and raised on a milk free diet. The mice were 3 weeks old at the start of the experiments.

b) Preparation of Tolerogenic Fractions

In order to be digested, β-LG (220 grams) was dissolved in bi-distilled water at 5% (w/w) final concentration. The β-LG was digested by TPCK treated trypsin, using an Enzyme/Substrate (E/S) ratio of 1/100 (w/w) at 40° C., pH 7.6 under constant stirring. After one hour hydrolysis, same amount of enzyme was added to give a 2/100 (w/w) final E/S ratio. After 4 hours hydrolysis, the reaction was stopped by inactivation of trypsin at 85° C. for 5 min. Total tryptic hydrolysate of β-lactoglobulin (TTH β-LG) was then lyophilized. The digested β-LG products were separated by preparative chromatography on a cationic resin.

15 different fractions were obtained, individually nanofiltered to concentrate and to eliminate salts, diafiltered, dialyzed, lyophilized and dry stored at room temperature until in vivo experiments.

Each fraction was further characterized by its peptide content using reverse phase High Performance Liquid Chromatography. Considering TTH β-LG as reference, enrichment and impoverishment of peptides in each fraction was appreciated by area detected at 214 nm using iso nitrogen injections.

c) Oral Tolerance Induction and Immunization Procedure

Gavages were orally administered to the mice at age 22 days, by gastric feeding of native β-LG (5 mg/g of body weight), various amounts of TTH β-LG, or various amounts of the different β-LG peptidic fractions. Control mice were fed saline water. 5 days later, all mice were immunized β-LG and OVA (Ovalbumin, grade V, Sigma), as a non-related antigen for testing the specificity of the immune response, 21 days after systemic challenge, a Delayed Type Hypersensitivity (DTH) evaluation was done by duplicate thickness measures of the left, rear footpad prior to, and following, immunization with β-LG.

d) Evaluation of the Immune Response 24 hours after DTH immunization, individual increases in foot pad thickness of those injected the day before were measured. Differences between these two measurements were expressed in <thickness (millimeters) and used in group comparisons. Then, from all mice, blood samples were obtained, spleens were taken and pooled according to group of treatment. Splenocyte specific proliferation assays were performed for each group. Intestinal contents were individually collected. Serum and intestinal samples were rapidly frozen at −80° C., until assays. Specific IgE against β-LG and against OVA were determined both in seric and intestinal samples.

e) Specific IgE Antibody Assays

Serum and intestinal fluid dilutions were assayed in duplicate for anti-β-LG and anti-OVA IgE antibodies by ELISA. Pooled samples from twenty non-immunized female mice were used as negative controls in each plates. Titers were determined by calculating the dilution of the sample that gave twice the absorbance of the negative control. Titers were expressed as the $\log_{10}$ of the reciprocal of the dilution.

f) Cell Cultures

Spleen cell solutions were homogenized and purified. Cells were cocultured in the presence of β-LG or of phytohaemagglutinin A. ($^3$H)Tdr (Amersham, Zurich) was added in the final 6 hours of culture and the plates were harvested and analyzed by scintillation counting. Stimulation indices were calculated as the ratio of blank-subtracted test and control values expressed as the mean cpm ($^3$H)Tdr incorporation by triplicate cultures.

g) Determination of β-LG IgG Binding Capacity

An ELISA inhibition was used to determine β-LG epitopes in β-LG hydrolysate and in β-LG fractions. β-lactoglobulin titers were calculated from a 5-fold dilution β-LG standard curve run on each plate.

DTH responses, seric and intestinal IgE responses were compared using ANOVA single factor tests.

Results a) Characterization of fractions obtained from TTH β-LG

In order to isolate the tolerogenic peptides from the TTH β-LG, large amounts of β-LG tryptic fractions have been produced by preparative chromatography. From each of them, 15 fractions (F1–F15) were collected and respectively pooled. The assigned sequences of β-LG tryptic peptides have been previously determined (see FIG. 2).

No specific peptide enrichment could be detected in fractions F1, F5 and F15.

3 different peptides T6, T17, and T18 present in fraction F2 were enriched: but were not concentrated in any of the other fractions.

Similarly, T7 was specifically enriched in fraction F6.

Apart from these peptides, concentrated in only one given fraction, some others were enriched in several fractions. This was the case for T2 1, for instance, clearly detected at high rates in fractions F7, F9, and F10, as shown below in Table 1.

TABLE 1

β-LG fraction masses and significant peptide enrichment within fractions.

| Fractions | F1 | F2 | F3 | F4 | F5 | F6 | F7 | F8 |
|---|---|---|---|---|---|---|---|---|
| Masses (g) | 52 | 13.9 | 11 | 11.8 | 2.57 | 1.94 | 4.37 | 13.1 |
| Significantly enriched peptides | — | T6 T17 T18 | T23 | T23 | — | T7 T9 | T20 T21 T24 | T9 T12 T24 |

| Fractions | F9 | F10 | F11 | F12 | F13 | F14 | F15 |
|---|---|---|---|---|---|---|---|
| Masses (g) | 5.01 | 6.53 | 1.05 | 3.46 | 1.9 | 2.67 | 28.8 |
| Significantly enriched peptides | T12 T21 | T10 T21 | T11 | T10 | T10 T11 | T10 T11 | — | b) Two Different Fractions of the β-LG Tryptic Hydrolysate Presented Tolerogenic Properties Fractions were pooled according to their enriched peptides similarities and in proportion to their respective masses, and then tested in vivo.

F1, F2, F5, and F15 were considered to be fed individually because they did not share peptide enrichment with the others fractions.

F3 and F4 were pooled based on high concentration of T23;

F8 and F9 were mixed to test the tolerogenic activity of T12;

F7 and F9 were pooled according to enrichment of T20 and T21;

F6, F11, F12, F13, and F14 were pooled together, each enriched in T9, T10, and T11.

Qualitative responses of the tolerogenic properties generated from feeding the different fraction groups at two different concentrations (0.5 or 0.125 mg/g of body weight) were evaluated. Induction or absence of induction of tolerogenic responses to β-LG has been determined by the statistical significance of the immune response.

Two of the eight tested fractions appeared to be active both in reducing seric anti-μ-LG IgE responses and β-LG specific splenocyte proliferation:

F2, when given orally at 0.125 mg/g of body weight,

F(7+9), at both tested doses.

c) Humoral, Mucosal and Cellular Tolerance Induced by Oral Administration of β-LG Tryptic Fractions F2 and F(7+9)

According to our quantitative criteria, seric and intestinal anti-β-LG IgE responses, DTH, and specific splenocyte proliferation, oral tolerance has been induced in mice fed either with F2 or with F(7+9) (FIG. 1).

For the two fraction fed groups, the seric anti-β-LG IgE titers, 3.58 +/−0.18 and 3.21+/−0.29 respectively for F2 and F(7+9), were not as low as when induced by TTH β-LG feeding (2.68+/−0.05) (FIG. 1A). However, specific levels of IgE were significantly lower than titers of control mice (4.16+/−0.05) ($p<0.05$). Specific intestinal IgE was also decreased in mice fed TTH β-LG (1.66+/−0.32) or fed the two βLG tryptic fractions (1.1+/−0.34 and 1.9+/−0.21 respectively for F2 and F(7+9)), assessing the orally induced down-regulation compared to the control group (2.32+/−0.64). FIG. 1B shows that specific DTH was clearly reduced in mice fed with either TTH β-LG (0.074 mm) or each of the two tolerogenic fractions (0.063 mm and 0.062 mm respectively for F2 and F(7+9)) in comparison to local hypersensitivity measured in control mice fed only with saline (0.164 mm).

To confirm the achieved induction of oral tolerance on cellular immunity, specific and non-specific splenocyte proliferation assays were performed. FIGS. 1C and D show that feeding mice either of the two elected β-LG fractions as well as TTH β-LG provoked a severe decrease of the proliferative response to β-LG in comparison to the one observed from splenocytes isolated from saline fed control mice. Indeed, stimulation indices were 0.225, 0.174, and 0.341, respectively for TTH β-LG, F2, and F(7+9) fed mice. As expected, the non-specific proliferative response due to PHA stimulation was not affected by the different feeding regimen.

d) Antigenicity of the β-LG Hydrolysate and β-LG Fractions

Measurement of residual β-LG epitopes performed for the different fractions by ELISA inhibition showed that mounts of β-LG epitopes present per g of proteins were highly different from one fraction to another, ranging from 15 μg/g of protein for F1 up to 9240 μg/g of protein for F13. These results also indicate that antigenic and tolerogenic sites might be distinctly located, suggesting that allergenicity and tolerogenicity could be uncoupled. Schematically, three different type of fractions can be described:

- a first type, represented by fraction F2, including basic peptides with a high tolerogenic potential associated to a very low antigenicity,
- at the other end, an F13 type fraction containing acidic peptides, highly antigenic and devoid of tolerogenic activity and, finally,
- in a median position, the peptides present in fractions F7 and F9 inducers of tolerance but still having notable antigenicity.

Fractions F2 and the mixture F(7+9) were both tolerogenic. Antigenicity of the tolerogenic fractions F2, F7 and F9 were lower than that of the total hydrolysate. Remarkably, the antigenicity of the tolerogenic F2 was found to be 53 times lower than the antigenicity of TTH β-LG. In these two tolerogenic fractions, the sizes of the potentially tolerogenic peptides were distributed between 8 amino acids for T6, and 23 amino acids for T21, given respective molecular weights between 915 and 2719 Da.

To be tolerogenic, peptides seem to require a precise balance between dose, size, sequence and structure. However, until now, correlation between peptide structure and tolerogenic properties has not been described in the literature.

Example 2

Obtention of Tolerogenic Peptides From Whey Protein

In order to obtain tolerogenic peptides, 1 kg of whey protein isolate was dissolved in 7 liters of water at 50° C. The pH was adjusted at 7.5 with 2N KOH. The volume was adjusted to 14 liters with water at 50° C. to obtain a 7% solution with respect of powder.

10 g of enzyme Trypsin+Chymotrypsin were added and the solution was allowed to hydrolysis during 120 min. The pH was maintained with an alkaline solution of 2N KOH and 2N NaOH. After the hydrolysis, the solution was heated to 80° C. during 10 min. The solution was cooled to 40° C. and ultrafiltered with 40,000 Da cut off membranes.

The clear permeate was treated by cationic resin conducted as followed in a final resin volume of about 180 ml. The resin was washed and equilibrated with 0.1N NaOH at a flow rate of 300 ml/h. 100 ml of clear permeate 40,000 Da were passed into the column. The non retained fraction was eluted by 540 ml of pure water. The second and the third were eluted by 900 ml of 0.5N HCl and 540 ml of 0.1N NaOH respectively.

The tolerogenic peptides are present in fraction F2 for example, in an amount sufficient to prevent from any reaction after DBPCFC performed with cow's milk.

Example 3

Obtention of Tolerogenic Peptides From Caseinates 1 kg of sodium caseinate was dissolved in 7 liters of water at 50° C. The pH was adjusted at 7.5 with 2N KOH. The volume was adjusted to 10 liters with water at 50° C. to obtain a 10% solution with respect of powder.

40 g of Alcalase enzyme were added and the solution was allowed to hydrolysis during 120 min. The pH was maintained with an alkaline solution of 2N KOH and 2N NaOH. Subsequent to the hydrolysis, the solution was heated to 80° C. during 10 min. The solution was cooled to 40° C. and ultrafiltered with 10,000 Da cut off polyethylsulfone membranes.

Reverse phase chromatography: 300 ml of the clear permeate were passed into the column equilibrated at a flow rate of 3 ml/min. The non retained fraction was eluted with 300 ml of water, then the second fraction was eluted with 200 ml of ethanol gradient 0–20%. Finally the third fraction was eluted with 200 ml of ethanol gradient 20–40%. The column was regenerated by 400 ml gradient ethanol 40–80% v/v and equilibrated with 500 ml of pure water.

Example 4

The procedure was as described in Example 3, except that the enzyme quantity and membrane cut off were changed by Alcalase 20 g and 40,000 Da respectively. The subsequent chromatography on cationic resin was conducted as followed: 150 ml of resin were washed 3 times by 500 ml of pure water then poured in a column which final resin volume was 180 ml. The resin was washed and equilibrated by 0.1N NaOH at a flow rate of 300 ml/h. 100 ml of clear permeate 40,000 Da were passed into the column at a flow rate of 300 ml/h. The non retained fraction was eluted by 540 ml of pure water. The second and the third ones were eluted by 900 ml of 0.5N HCl and 540 ml of 0.1N NaOH respectively.

Example 5

The procedure was as described in Example 3, except that the reverse phase treatment was changed by a chromatography on a strong anionic resin as followed: 150 g of resin were washed 3 times by 500 ml of pure water, then poured in a column where the resin was washed and equilibrated with 0.1N HCl at a flow rate of 180 ml/h. 100 ml of clear ultra filtrate were passed into the column at a flow rate of 180 ml/h. The non retained fraction was eluted with 540 ml of water. The second and the third ones were eluted by 3 column volumes of 0.5N NaOH and 5 column volumes of 0.1N HCl respectively.

Example 6

Tolerogenic Infant Formula

The tolerogenic peptides T6 and T17 contained in tolerogenic fraction F2 were synthetically prepared. T13 contained in a non tolerogenic fraction was also synthesized as a negative control. Oral tolerance induction of these peptides were tested in rats mice as described in example 1c) except that the dose is of 20 mcg/g of body weight.

Results are shown below in Table 2.

| Peptides | tolerized anti-LG IgE/ control | Stimulation index (rate) | Stimulation index (GLM) |
|---|---|---|---|
| T17 | 2.67/3.39 | 0.305 | 0.405 |
| T6 | 3.24/3.39 | 0.53 | 0.285 |
| T6–T17 (linked) | 3.40/3.39 | 0.92 | 0.81 |
| T13 (negative control) | 3.20/3.39 | 1.7 | 0.87 |

The oral administration of T6 or T17 induces a cellular tolerance (specific inhibition of lymphocyte proliferation). T6 T17 also induces a humoral tolerance by significantly decreasing specific anti-β-LG IgE.

The oral administration of T13 (negative control) do not induce any tolerance.

These two peptides T6 ($H_2N$-I-D-A-L-N-E-N-K-COOH) and T17 ($H_2N$-V-L-V-L-D-T-D-Y-K,-K-COOH) have a high tolerogenic potential associated to a very low antigenicity. They can be used in food or pharmaceutical composition for inducing a protein tolerance in at risk individuals of protein allergy.

Example 7

Tolerogenic Infant Formula

The composition for 100 g of powder contains 12.5% of peptides (synthesized peptides T6 or T17 or tolerogenic peptides as prepared in Example 2, represent about 0.1 to 0.2% of total peptides), 26% of fats, 56% carbohydrates (including lactose 39%, maltodextrin 11%, starch 6%), traces of vitamins and oligoelements to meet daily requirements, 2.5% minerals and 3% moisture.

13 g of this powder is mixed in 100 ml of water. The obtained composition is an infant formula particularly intended for at risk infant to cow's milk allergy.

Example 8

Tolerogenic Infant Formula

In order to obtain a tolerogenic infant formula, we prepare the following mixture containing, for 100 ml of formula, 1.6% peptides (tolerogenic peptides as prepared in example 2, represent about 0.1 to 0.2% of total peptides), 3.4% fat, 7.4% carbohydrates (including lactose 5.2%, maltodextrin 1.4%, starch 0.8%), traces of vitamins and oligoelements to meet daily requirements, 0.3% of minerals and 79.9% of water.

Example 9

In order to obtain a tolerogenic preparation of a small volume, we prepared the following mixture containing, for 30 ml of preparation, from about 0.003% to about 0.015% of tolerogenic peptides (tolerogenic peptides, as prepared in Example 2, represent 100% of total peptides), 7.4% of carbohydrates (including maltodextrin 1.4% and saccharose 6%), 92.5% of water and aroma. In order to induce oral tolerance, this preparation is to be administered 1 to 5 times daily to newborns at risk of cow's milk allergy either fed hypoallergenic formula or breastfed.

What is claimed is:

1. A hypoallergenic composition for the induction of protein tolerance in at risk individuals of protein allergy, containing (i) an extensively hydrolyzed protein material or (ii) a free amino acid basis to form a "non-allergenic" base composition, wherein the base composition further includes, as an active ingredient, at least one tolerogenic peptide of the allergenic protein in the form of (i) one or more isolated tolerogenic peptidic fraction(s) resulting from the hydrolysis of proteinaceous material containing the allergenic protein and in an amount to provide a ratio of tolerogenic response to residual antigenicity of at least about $2 \times 10^{-2}$, wherein native protein residual antigenicity is $10^6$ and a tolerogenic response is 1, or (ii) one or more synthetically prepared tolerogenic peptide(s), the tolerogenic peptide being in an amount sufficient to induce oral tolerance.

2. The composition of claim 1, which contains an amount of tolerogenic peptide of about 0.01% to 10% of the total nitrogen source of the proteins in the composition.

3. The composition of claim 1, which contains an amount of tolerogenic peptide of about 0.1% to 0.2% of the total nitrogen source of the proteins in the composition.

4. The composition of claim 1, wherein the tolerogenic peptidic is one or more peptide fractions comprising $H_2N$-I-D-A-L-N-E-N-K-COOH, $H_2N$-V-L-V-L-D-T-D-Y-K,-K-COOH or $H_2N$-T-P-E-V-D-D-E-A-L-E-K-F-D-K-COOH from β-lactoglobulin.

5. The composition of claim 1, which further comprises a source of nitrogen providing 7 to 25% of the total energy, a source of carbohydrates which provides 28 to 66% of the total energy, a source of lipids which provides 25 to 60% of the total energy, minerals and vitamins to meet daily requirements and at least one of the tolerogenic peptides that is added in an efficient quantity so as to induce oral tolerance.

6. A method for the preparation of a hypoallergenic composition intended for administration to mammals susceptible to cow's milk allergy, comprising preparing a free amino acid base or an extensively hydrolyzed protein material to form a "non-allergenic base composition and incorporating into the non-allergenic base composition, at least one isolated tolerogenic peptide fraction or at least one synthetically prepared tolerogenic peptide of a milk protein in an amount sufficient to induce tolerance to milk proteins.

7. The method of claim 6, wherein the tolerogenic peptide is at least one tolerogenic peptide of the allergenic protein.

8. The method of claim 6, wherein the tolerogenic peptide is from milk origin.

9. The method of claim 8, wherein the tolerogenic peptide is from β-lactoglobulin, α-lactalbumin, bovin serum albumin or casein origin.

10. The method of claim 6, wherein the tolerogenic peptide comprises: $H_2N$-I-D-A-L-N-E-N-K-COOH, $H_2N$-V-L-V-L-D-T-D-Y-K,-K-COOH or $H_2N$-T-P-E-V-D-D-E-A-L-E-K-F-D-K-COOH from β-lactoglobulin.

11. The method of claim 6, wherein the composition contains a source of nitrogen which provides 7 to 25% of the total energy, a source of carbohydrates which provides 28 to 66% of the total energy, a source of lipids which provides 25 to 60% of the total energy, and, optionally, minerals and vitamins to meet daily requirements.

12. The method of claim 11, wherein the effective amount of the tolerogenic peptide is at least about 0.01% to 10% of the total nitrogen source of the protein.

13. The method of claim 6, wherein the isolated tolerogenic peptide fraction is in an amount to provide a ratio of tolerogenic response to residual antigenicity of at least about $2 \times 10^{-2}$, wherein native protein residual antigenicity is $10^6$ and a tolerogenic response is 1.

14. The method of claim 6, wherein the tolerogenic peptide comprises $H_2N$-I-D-A-L-N-E-N-K-COOH, $H_2N$-V-L-V-L-D-T-D-Y-K,-K-COOH or $H_2N$-T-P-E-V-D-D-E-A-L-E-K-F-D-K-COOH from β-lactoglobulin.

15. The method of claim 6, wherein the hypoallergenic composition includes a source of nitrogen providing 7 to 25% of the total energy, a source of carbohydrates which provides 28 to 66% of the total energy, a source of lipids which provides 25 to 60% of the total energy, minerals and vitamins to meet daily requirements and at least one of the tolerogenic peptides that is added in an efficient quantity so as to induce oral tolerance.

16. A method of preparing the composition of claim 1, comprising preparing the hypoallergenic compositions containing the extensively hydrolyzed "non allergenic" protein material or the free amino acid basis and incorporating into such composition, as the active ingredient at least one tolerogenic peptide.

* * * * *